(12) United States Patent
Lee et al.

(10) Patent No.: US 10,899,791 B2
(45) Date of Patent: Jan. 26, 2021

(54) METHOD FOR SYNTHESIZING ETELCALCETIDE OR SALTS THEREOF

(71) Applicant: Chunghwa Chemical Synthesis & Biotech Co. Ltd., New Taipei (TW)

(72) Inventors: Kwang-Chung Lee, New Taipei (TW); Kuang-Chan Hsieh, New Taipei (TW); Hui-Wen Cheng, New Taipei (TW); Chia-Sui Kao, New Taipei (TW); Ya-Ling Huang, New Taipei (TW); Wei-Ssu Wang, New Taipei (TW)

(73) Assignee: CHUNGHWA CHEMICAL SYNTHESIS & BIOTECH CO. LTD, New Taipei (TW)

( * ) Notice: Subject to any disclaimer, the term of this patent is extended or adjusted under 35 U.S.C. 154(b) by 48 days.

(21) Appl. No.: 16/137,967

(22) Filed: Sep. 21, 2018

(65) Prior Publication Data

US 2019/0100554 A1    Apr. 4, 2019

(30) Foreign Application Priority Data

Oct. 3, 2017 (TW) .............................. 106134261 A

(51) Int. Cl.
C07K 1/04 (2006.01)
C07K 7/06 (2006.01)
C07K 1/06 (2006.01)

(52) U.S. Cl.
CPC ................ *C07K 1/04* (2013.01); *C07K 1/061* (2013.01); *C07K 7/06* (2013.01)

(58) Field of Classification Search
None
See application file for complete search history.

(56) References Cited

FOREIGN PATENT DOCUMENTS

WO    WO-2015154031 A1 * 10/2015  ............... C07K 7/06
WO    WO-2017114240 A1 *  7/2017  ............... C07K 1/04

OTHER PUBLICATIONS

Protein Technologies, Inc., "Introduction to Fmoc Solid Phase Peptide Synthesis", pp. 1-6, 2006 (Year: 2006).*

* cited by examiner

*Primary Examiner* — Lianko G Garyu
(74) *Attorney, Agent, or Firm* — Muncy, Geissler, Olds & Lowe, P.C.

(57) ABSTRACT

The present invention provides a method for synthesizing etelcalcetide or salts thereof, comprising the steps of: (a) synthesizing the D-amino acids in the formula (I) sequentially by Fmoc solid-phase synthesis, using a solid support as a starting material in solid phase peptide synthesis and sequentially synthesizing a D-form amino acid of formula (I) by Fmoc chemistry; deprotecting Fmoc group and acetylating the amino group to obtain a sequence A comprising protecting groups (PG) in the side chain of D-Cys and D-Arg; (b) removing the protecting group in the side-chain of D-Cys of the sequence A to form a sequence B; (c) disulfide formation at D-Cys of the sequence B by (PG)-L-Cys-OH to obtain a sequence C; (d) using a cleavage solution to remove the protecting groups of the sequence C to give etelcalcetide as formula (I). The present invention can shorten the steps and time for preparing Etelcalcetide.

12 Claims, 1 Drawing Sheet

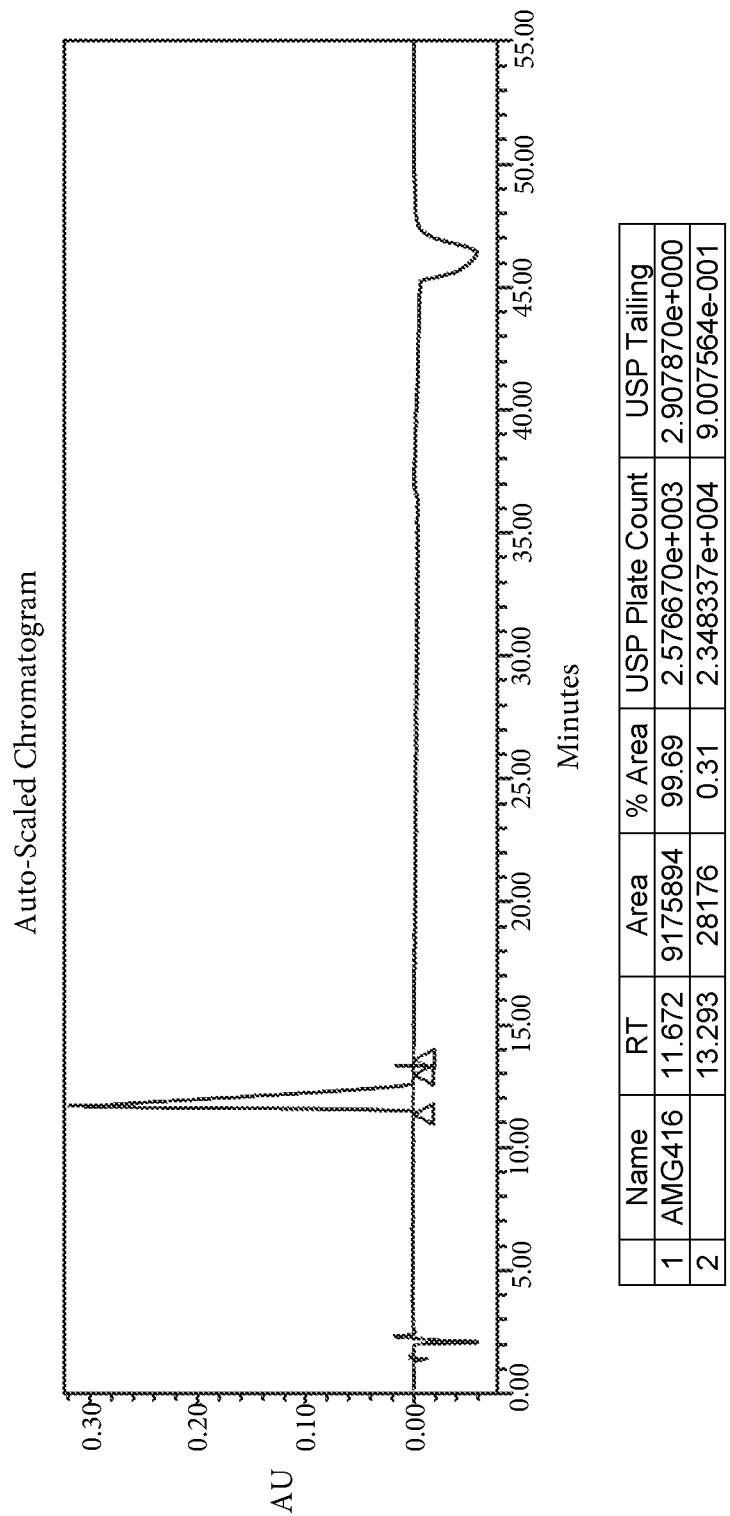

METHOD FOR SYNTHESIZING ETELCALCETIDE OR SALTS THEREOF

BACKGROUND OF THE INVENTION

1. Technical Field

The present invention relates to a method of peptide synthesis regarding an etelcalcetide production as an inhibitor of calcium-sensing receptors.

2. Description of Related Art

Being in a state of kidney failure to a low calcium and high phosphate concentration in blood and lack of active vitamin D3 substantially secretes parathyroid hormone (PTH) to stabilize physiological function. In contrast, people having hypersecretory parathyroid hormone means kidney is not working normally as a result of secondary hyperparathyroidism.

Calcium is released from bone tissue while parathyroid substantially secreted to be a calcium-rich blood and calcium resorption in kidney. However, calcitonin secreting by thyroid gland functionalizes calcium-free blood due to resorption in bone tissue.

Patient suffered from kidney disease slightly releases phosphate to lower calcium concentration which substantially induces the calcium-sensing receptor (CaSR) and the CaSR secretes parathyroid hormone as a result of improvement of vitamin D3 absorption in intestine. In addition, the PTH alternatively releases calcium from bone tissue, composing of calcium phosphate, to normalize the phosphate concentration in blood.

Both of etelcalcetide and cinacalcet are CaSR inhibitors. EC50 to cinacalcet is superior to etelcalcetide as low as 1000 fold, nevertheless, concentration of etelcalcetide, which has a significant first-pass effect and low metabolism in P450, would not be greatly reduced before it reaches to CaSR. Therefore, the daily dose of etelcalcetide is 2.5 to 10 mg, which is lower than that of cinacalcetide as 30 mg.

BRIEF SUMMARY OF THE INVENTION

Peptide synthesis is a general way in the solid and liquid process. In the liquid process, it needs lots of steps in purification and recrystallization to remove starting material and side product resulting in a low yield and a long time in total process. Meanwhile, etelcatcetide synthesis in a known process proceeds many steps of purification, production process, and time so as to lower yield and increase cost.

Thus, this invention is a way to process etelcalcetide and its counterion. It has a high purity and yield while the process follows by solid phase peptide synthesis in the presence of purification in one step.

The primary object of the present invention is to provide a method for synthesizing etelcalcetide (of the following formula (I)) or salts thereof, comprising the steps of:

(a) using a solid support as a starting material in solid phase peptide synthesis and sequentially synthesizing a D-form amino acid of formula (I) by Fmoc chemistry; deprotecting Fmoc group and acetylating the amino group to obtain a sequence A comprising protecting groups (abbreviated as PG in the following sequence A) in the side chain of D-Cys and D-Arg:

```
(A);
Ac-D-Cys(PG)-D-Ala-D-Arg(PG)-D-Arg(PG)-D-Arg-(PG)-
D-Ala-D-Arg(PG)-solid support
```

(b) removing the protecting group in the side-chain of the D-Cys of the sequence A to form the sequence B:

```
(B);
Ac-D-Cys-D-Ala-D-Arg(PG)-D-Arg(PG)-D-Arg-(PG)-D-
Ala-D-Arg(PG)-solid support
```

(c) disulfide formation at D-Cys of the sequence B by (PG)-L-Cys-OH to obtain a sequence C:

```
(C);
  Ac-D-Cys-D-Ala-D-Arg(PG)-D-Arg(PG)-D-Arg-(PG)-D-Ala-D-Arg(PG)-solid support
  |
(PG)-L-Cys-OH
``` and (d) using a cleavage solution to remove the protecting group of the sequence C to obtain etelcalcetide as the formula (I):

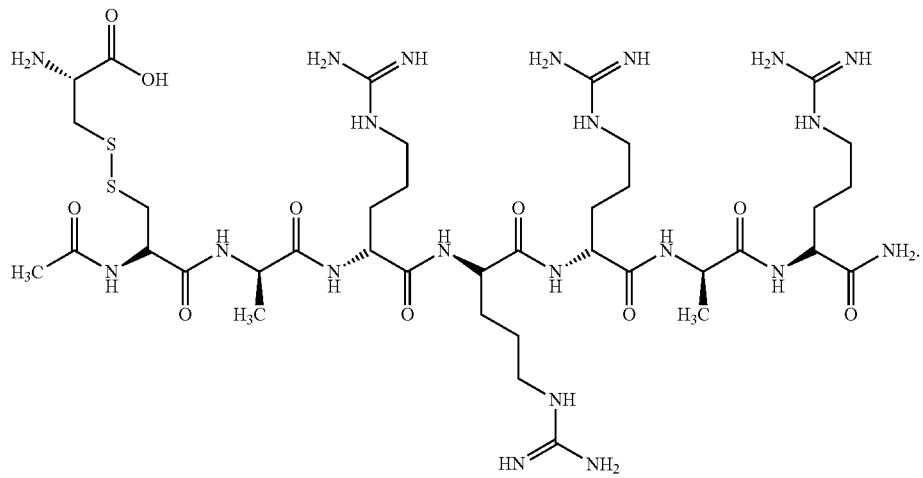

Further, the solid support is selected from the group consisting of: Rink amide resin, Rink amide AM resin, Rink amide MBHA resin, Wang resin, and 2-Chlorotrityl chloride resin with a loading ratio as 0.1-1.5 mmol/g.

Further, the side-chain protecting group of the D-Cys is 4-methyltrityl (Mtt), and the side-chain protecting group of the D-Arg is 2,2,4,6,7-pentamethyl-dihydro-benzofuran-5-sulfonyl (Pbf).

Further, the step (a) further comprises using a coupling reagent, which is selected from O-(benzotriazol-1-yl)-N,N,N',N'-tetramethyluronium tetrafluoroborate (TBTU), N,N'-diisopropylcarbodiimide (DIC), 1-hydroxybenzotriazole hydrate (HOBt), O-(benzotriazol-1-yl)-N,N,N',N'-tetramethyluronium hexafluorophosphate (HBTU), O-(6-chlorobenzotriazol-1-yl)-N,N,N',N'-tetramethyluronium hexafluorophosphate (HCTU), benzotriazol-1-yl-oxytripyrrolidinophosphonium hexafluorophosphate (PyBOP), or benzotriazol-1-yloxytris(dimethylamino)phosphonium hexafluorophosphate (BOP).

Further, the step (a) further comprises using a base solution, which is selected from the group consisting of: dimethylformamide (DMF), N-methyl-2-pyrrolidone (NMP), diisopropylethylamine (DIPEA), N-methylmorpholine (NMM), trimethylamine (TEA), pyridine, and the combination thereof.

Further, a deprotection solution is used for deprotecting Fmoc group, wherein the deprotection solution is selected from piperidine, diethylamine (DEA), or morpholine preparing in dimethylformamide (DMF), N-methyl-2-pyrrolidone (NMP), or dimethyl sulfoxide (DMSO) with a concentration ranging from 5% to 30%.

Further, an acetylation reagent with an equivalent ranging from 1 to 500 is added with pyridine for acetylating the amine group, wherein the acetylation reagent is selected from acetic anhydride ($Ac_2O$) or acetyl chloride prepared in dimethylformamide (DMF), N-methyl-2-pyrrolidone (NMP), or dimethyl sulfoxide (DMSO), and wherein the pyridine is of an equivalent ranging from 1 to 500.

Further, an acid solution comprises trifluoroacetate (TFA), thioanisole, triisopropylsilane (TIPS), and methylene dichloride (DCM) is added in the step (b) to remove the protecting group of the side chain of D-Cys of the sequence A.

Further, the step (c) further comprises using a synthesis solution selected from the group consisting of: diisopropylethylamine (DIPEA), N-methylmorpholine (NMM), and trimethylamine (TEA) prepared in dimethylformamide (DMF) or N-methyl-2-pyrrolidone (NMP).

Further, the protecting group in N-terminal of L-Cys is t-butyloxycarbonyl (Boc) or fluorenylmethyloxycarbonyl (Fmoc), and the protecting group in the side-chain of L-Cys is 3-nitro-2-pyridinesulphenyl (Npys) 4-methyltrityl (Mtt), trityl (Trt), acetaminomethyl (acm), methylcarboxamide (cam), diphenylmethyl (Dpm), 4-methoxybenzyl (Mob), S-tert-butylthio (StBu), methyl (me), sulfo ($SO_3H$), 2,4,6-trimethoxyphenylthio (STmp) or methylcarboxamide.

Further, the cleavage solution in the step (d) comprises triisopropylsilane (TIPS), thioanisole, trifluoroacetate (TFA), and $H_2O$.

Further, etelcalcetide is further added into a 0.01-10% HCl solution to form etelcalcetide hydrochloride.

Etelcalcetide synthesis and its counterion production of the present invention relate to compress process and time in order to increase efficiency to produce high purity and yield. This method provides an inhibitor of calcium-sensing receptor against secondary hyperparathyroidism. Thus, this invention is a reliable process in substantial production to produce high quality of etelcalcetide active pharmaceutical ingredients (APIs) and formulation thereof.

BRIEF DESCRIPTION OF THE SEVERAL VIEWS OF THE DRAWINGS

FIG. 1 is a chromatogram of high performance liquid chromatographic (HPLC) of etelcalcetide hydrochloride (etelcalcetide HCl) in accordance with a preferred embodiment of the present invention.

DETAILED DESCRIPTION OF THE INVENTION

A detailed description and the technical contents of the present invention are given below with reference to the accompanying drawings. Furthermore, for easier illustrating, the drawings of the present invention are not a certainly the practical proportion and are not limited to the scope of the present invention.

The use of "or" means "and/or" unless stated otherwise. The use of "comprise" means not excluding the presence or addition of one or more other components, steps, operations, or elements to the described components, steps, operations, or elements, respectively. Similarly, "comprise," "comprises," "comprising" "include," "includes," and "including" are interchangeable and not intended to be limiting. As used herein and in the appended claims, the singular forms "a," "an," and "the" include plural referents unless the context dictates otherwise. The terms "a", "an," "the," "one or more," and "at least one," for example, can be used interchangeably herein. The terms "about", "approximately", or "substantially" means having a value or range that is close to the allowable specified error to avoid any unreasonable third party illegally or unfairly using from understanding the precise or absolute value disclosed herein.

The present invention provides a method for synthesizing etelcalcetide (of the following formula (I)) or salts thereof, comprising the steps of: (a) using a solid support as a starting material in solid phase peptide synthesis and sequentially synthesizing a D-form amino acid of formula (I) by Fmoc chemistry; deprotecting Fmoc group and acetylating the amino group to obtain a sequence A comprising protecting groups (abbreviated as PG in the following sequence A) in the side chain of D-Cys and D-Arg:

(A);

Ac-D-Cys(PG)-D-Ala-D-Arg(PG)-D-Arg(PG)-D-Arg-(PG)-

D-Ala-D-Arg(PG)-solid support (b) removing the protecting group in the side-chain of D-Cys of the sequence A to form a sequence B:

(B);

Ac-D-Cys-D-Ala-D-Arg(PG)-D-Arg(PG)-D-Arg-(PG)-D-

Ala-D-Arg(PG)-solid support (c) disulfide formation at D-Cys of the sequence B by (PG)-L-Cys-OH to obtain a sequence C:

(C);
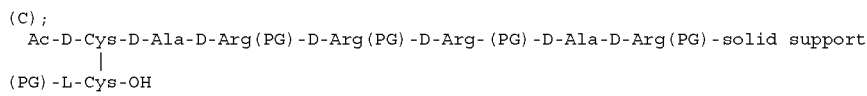

and (d) using a cleavage solution to remove the protecting groups of the sequence C to obtain etelcalcetide of the formula (I):

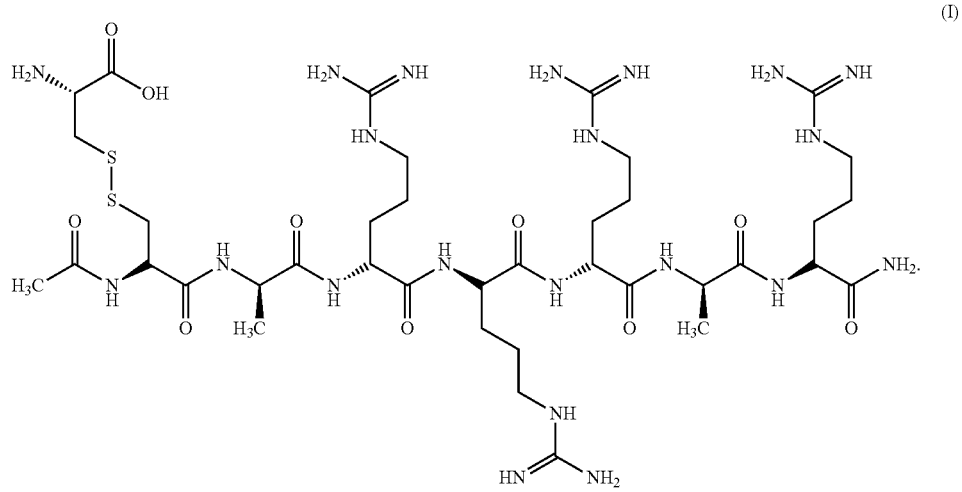

As used herein, the term "etelcalcetide" refers to a calcimimetic and CaSR that includes seven D-amino acids bonded to an L-cysteine through a disulfide bond to produce the structure shown in formula (I).

As used herein, the term "solid-phase (peptide/polypeptide) synthesis" refers to a method of organic chemistry for synthesizing peptides/polypeptides and proteins. The solid support having a structural porosity and insoluble in water is subjected to conjugate with polypeptide; therefore, it removes starting materials, side products, and solvent by filtration, and the polypeptide conjugated with the solid support is remained. This invention refers to a solid phase peptide synthesis following by Fmoc chemistry, wherein Fmoc group (9-fluorenylmethoxycarbonyl group), as a N-terminal protecting group, is subjected to deprotect in the presence of piperidine without any effect of acid-treating release in the protecting group of the side chain. This is a continuously synthetic process without further purification in each intermediates.

As used herein, the term "solid support" refers to a polymer carrier for use in solid-phase synthesis of polypeptides. The solid support refers to a resin or other polymer substances having porous-rich solid and solubility-poor ability. In one preferred embodiment, the solid support used in the methods for synthesizing etelcalcetide or salts of the present invention is an amine-free solid support. The known resins are poly(styrene-co-divinylbenzene), polyacrylamides, polyethylene glycol-based resins, and their derivatives. The resins are subjected to introduce a functional group such as chloromethyl, carboxyl, amino, or hydrazide. In one embodiment, the solid support in the present invention can be rink amide, rink amide AM, rink amide MBHA, rink amide PEGA, wang, 2-chlorotrityl chloride, or their derivatives or analogs. In one embodiment, the terminal of the solid support is amine-functionalized type which have a substitution ratio ranges between 0.1-1.5 mmol/g, e.g., 0.1 mmol/g, 0.3 mmol/g, 0.5 mmol/g, 0.7 mmol/g, 1.0 mmol/g, 1.3 mmol/g, or 1.5 mmol/g.

As used herein, the term "coupling reagent" refers to be an additive in which two starting materials are reacted together and particularly used in solid phase peptide synthesis named a coupling reaction or condensation. In one embodiment, a carbodiimide-based reagent as the coupling reagent in the present invention includes, but not limited to, N,N'-dicyclohexylcarbodiimide (DCC), N,N'-diisopropylcarbodiimide (DIC), 1-(3-dimethylaminopropyl)-3-ethylcarbodiimide hydrochloride (EDC), 1-hydroxybenzotriazole hydrate (HOBt), or any other carbodiimide-derived reagents. A phosphonium-based reagent as the coupling reagent in the present invention includes, but not limited to, benzotriazol-1-yloxytris(dimethylamino)phosphonium hexafluorophosphate (BOP), benzotriazol-1-yl-oxytripyrrolidinophosphonium hexafluorophosphate (PyBOP), (7-azabenzotriazol-1-yloxy)tripyrrolidinophosphonium hexafluorophosphate (PyAOP), bromotripyrrolidinophosphonium hexafluorophosphate (PyBrOP), or bis(2-oxo-3-oxazolidinyl)phosphinic chloride (BOP-Cl). A uronium-based reagent as the coupling reagent in the present invention includes, but not limited to, O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), or O-(6-chlorobenzotriazol-1-yl)-N,N,N',N'-tetramethyluronium hexafluorophosphate (HCTU). Efficiency-promoted coupling reagents are additives which are further used including, but not limited to, N-hydroxysuccinimide (HOSu), HOBt, 1-hydroxy-7-azabenzotriazole (HOAt), 3-hydroxy-1,2,3-benzotriazin-4 (3H)-one (HOOBt), N-hydroxysuccinimide (NHS), or N-hydroxysulfosuccinimide (sulfo-NHS). In a preferred embodiment, TBTU, DIC, HOBt, HBTU, HCTU, PyBOP, or BOP are one of coupling reagents in the step (a) of the present invention.

As used herein, the term "base solution" refers to a solution generally used in solid phase peptide synthesis to produce an alkaline environment. In a preferred embodiment, the base solution includes, but not limited to, dimethylformamide (DMF), N-methyl-2-pyrrolidone (NMP), diisopropylethylamine (DIPEA), N-methylmorpholine (NMM), triethylamine (TEA), or their combination in the step (a) of the present invention. In a more preferred embodiment, a combination of DIPEA and NMP are those in which base solution generally used in the step (a) of the present invention.

In one preferred embodiment, the base solution used in the step (c) of the present invention includes, but not limited to, diisopropylethylamine (DIPEA), N-methylmorpholine (NMM), trimethylamine (TEA), or their combination and prepared in dimethylformamide (DMF) or N-methyl-2-pyrrolidone (NMP). In a more preferred embodiment, a combination of TEA and NMP are those in which base solution generally used in the step (c) of the present invention.

As used herein, the term "deprotection solution" refers to a base solution generally used to deprotect protecting group in solid phase peptide synthesis, and the deprotection solution used in the step (a) of the present invention includes, but not limited to, piperidine, diethylaminoe (DEA) or morpholine, prepared in dimethylformamide (DMF), N-methyl-2-pyrrolidone (NMP), or dimethyl sulfoxide (DMSO). In a more preferred embodiment, a combination of piperidine and NMP are those in which concentration ranging from 5 to 30%, e.g., 5%, 7%, 10%, 13%, 15%, 17%, 20%, 23%, 25%, 27%, or 30%, generally used in the step (a) of the present invention. In a more preferred embodiment, the deprotection solution of the present invention has a ratio of 20% of piperidine and NMP.

As used herein, the term "acetylation" refers to end of reaction by introducing an acetyl group to a structure in solid phase peptide synthesis. In a preferred embodiment, either acetic anhydride ($Ac_2O$) or acetyl chloride are those in which preparation in dimethylformamide (DMF), N-methyl-2-pyrrolidone (NMP), or dimethyl sulfoxide (DMSO), which is used as an acetylation reagent in the step (a), is generally used in solid phase peptide synthesis, wherein the acetylation reagent has an equivalent of acetyl groups ranging from 1 to 500, e.g. 1, 5, 10, 50, 100, 150, 200, 250, 300, 350, 400, 450, or 500 equivalents; further, the acetylation reagent is added with pyridine with an equivalent ranging from 1 to 500 for acetylating the amine group.

As used herein, the term "acidic solution" refers to a solution generally used in solid phase peptide synthesis to produce an acidic environment. In a preferred embodiment, a composition of trifluoroacetate (TFA), thioanisole, and triisopropylsilane (TIPS), which is used as an acidic solution, is subject to deprotect protecting group in a side chain of D-Cys in the step (b) of the present invention. In another preferred embodiment, the acidic solution includes 1%-15% (e.g., 1%, 2%, 3%, 4%, 5%, 6%, 7%, 8%, 9%, 10%, 11%, 12%, 13%, 14%, or 15%) TFA, 1%-10% (e.g., 1%, 2%, 3%, 4%, 5%, 6%, 7%, 8%, 9%, or 10%) thioanisole, and 1%-15% (e.g., 1%, 2%, 3%, 4%, 5%, 6%, 7%, 8%, 9%, 10%, 11%, 12%, 13%, 14%, or 15%) TIPS. In a more preferred embodiment, an acidic solution consists of TFA, TIPS, thioanisole, and methylene dichloride (DCM), wherein TFA, TIPS, thioanisole, and DCM have a percentage (in volume) of 3, 10, 2.5, 84.5, respectively, in the step (b) of the present invention.

As used herein, the term "cleavage solution" refers to a solution generally used to deprotect protection group or cleavage solid support in solid phase peptide synthesis. In one embodiment, the cleavage solution comprises TIPS, 1,2-ethanedithiol (EDT), thioanisole, and/or TFA. In a preferred embodiment, the cleavage solution includes TIPS, thioanisole, and TFA. In another preferred embodiment, the cleavage solution includes 1%-15% (e.g., 1%, 2%, 3%, 4%, 5%, 6%, 7%, 8%, 9%, 10%, 11%, 12%, 13%, 14%, or 15%) TIPS, 1%-10% (1%, 2%, 3%, 4%, 5%, 6%, 7%, 8%, 9%, or 10%) thioanisole, and 75%-99% (e.g., 75%, 77%, 79%, 81%, 83%, 85%, 87%, 89%, 91%, 93%, 95%, 97%, or 99%) TFA. In a more preferred embodiment, the cleavage solution consist of TFA, TIPS, thioanisole, and $H_2O$, wherein TFA, TIPS, thioanisole, and $H_2O$ have a percentage (in volume) of 85, 10, 2.5, 2.5, respectively.

As used herein, the term "D-amino acids" refers to D-Cys, D-Ala, and D-Arg which were used in etelcalcetide synthesis process, wherein D-Cys and D-Arg are each provided with protecting group(s) in a side chain. In a preferred embodiment, the protecting group in the side chain of D-Cys is 4-methyltrityl (Mtt), trityl (Trt), acetaminomethyl (acm), 3-nitro-2-pyridinesulphenyl (Npys), methylcarboxamide (cam), diphenylmethyl (Dpm), 4-methoxybenzyl (Mob), S-tert-butylthio (StBu), methyl (me), sulfo ($SO_3H$), 2,4,6-trimethoxyphenylthio (STmp) or methylcarboxamide, and the protecting group of in the side chain of D-Arg is 2,2,4,6,7-pentamethyl-dihydro-benzofuran-5-sulfonyl (Pbf), tert-butoxycarbonyl (Boc), allyloxycarbonyl (Alloc), methyl (me), benzyloxycarbonyl (Z or Bz), 1,2-dimethylindole-3-sulfonyl (MIS), 2,2,5,7,8-pentamethylchroman-6-sulfonyl (Pmc), mesitylene-2-sulfonyl (Mts), or 4-methoxy-2,3,6-trimethylbenzenesulfonyl (Mtr). In a more preferred embodiment, D-amino acids used in etelcalcetide synthesis are Fmoc-D-Cys(Mt)-OH, Fmoc-D-Arg(Pbf)-OH, and Fmoc-D-Ala-OH.

As used herein, the term "L-Cys" refers to L-type of cysteines used in etelcalcetide synthesis of the present invention for formation of disulfide bond at a side chain. In a preferred embodiment, the protecting group in N-terminal of L-Cys is t-butyloxycarbonyl (Boc) or fluorenylmethyloxycarbonyl (Fmoc), and the protecting group in a side chain of L-Cys is 3-nitro-2-pyridinesulphenyl (Npys) 4-methyltrityl (Mtt), trityl (Trt), acetaminomethyl (acm), methylcarboxamide (cam), diphenylmethyl (Dpm), 4-methoxybenzyl (Mob), S-tert-butylthio (StBu), methyl (me), sulfo ($SO_3H$), 2,4,6-trimethoxyphenylthio (STmp) or methylcarboxamide. In a more preferred embodiment, the protecting group in N-terminal of L-Cys is t-butyloxycarbonyl (Boc) or fluorenylmethyloxycarbonyl (Fmoc), and the protecting group in a side chain of L-Cys is 3-nitro-2-pyridinesulphenyl (Npys), wherein L-Cys has an equivalent rangings from 1 to 50, e.g. 1, 5, 10, 15, 20, 25, 30, 35, 40, 45, or 50.

The present invention also provides a method for synthesizing etelcalcetide salts (or counterions). More specifically, the present invention develops a method on etelcalcetide as a complex of biocompatible salts. These counterions include, but are not limited to, hydrochlorides, hydrobromides, sulfates, bisulfates, phosphates, nitrates, acetates, valerates, stearates, benzoates, and tosylates. In one embodiment, etelcalcetide is subjected to introduce into a HCl solution, which has a concentration of 0.01-10%, and then a mixed solution is obtained with a concentration of etelcalcetide ranging from 0.5 to 66 mg/mL, and the mixed solution is lyophilized to produce etelcalcetide hydrochloride. In one embodiment, the hydrochloric acid is prepared as a pH value of 0.5, 0.7, 1, 1.3, 1.5, 1.7, or 2. In another embodiment, the concentration of a mixed solution having etelcalcetide and hydrochloride is 0.5 mg/mL, 1 mg/mL, 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, or 66 mg/mL.

The present invention is more detailed illustrated in the examples below which are not intended to be limited.

Fmoc Solid Phase Peptide Synthesis

Peptide is synthesized using standard Fmoc-strategy with conjugation of amino acid in solid support and initial purification by filtration and wash. After synthesizing a sequence with desired linear amino acids, the formation of disulfide bond(s) was conducted for obtaining a desired structure.

Generally, the solid support, e.g. a rink amide resin, was weighed into the reaction vessel and swelled with freshly DMF or NMP (100 mL) for 1 hr to expose the reaction site of the solid support prior to synthetic process. After filtering out DMF or NMP, the Fmoc protecting groups on the solid support or on a coupled amino acid(s) were removed with 20% piperidine dissolved in DMF or NMP as a deprotection solution and this process was monitored with UV-Vis spectroscopy. Once the deprotection reaction completed, the resin (i.e., the solid support) was washed with NMP or DMF for the next step.

Then, the solid support, i.e., Fmoc-free rink amide resin obtained by the aforementioned processes, was mixed and reacted with a solution consisted of amino acids, a base, a coupling reagent, and NMP, as a solvent, at room temperature. The reaction was monitored by the results of Kaisar test. In details, after adding Kaiser reagents, for example, 20 uL of each solution of 0.28 M ninhydrin/ethanol, 42.37 M phenol/ethanol, and pyridine, into the solid support, the mixture was heated to 120° C. for four minutes. The aforesaid solid support and solutions with a free primary amine was indicated by blue resin (a positive result, means that amino acid synthesis reaction was not over), otherwise the resin is achromatic or yellowish (a negative result, means that amino acid synthesis reaction was over).

The foregoing step is repeated until a linear peptide of the desired sequence is completed. After that, the Fmoc protecting group at the N-terminal of the linear peptide is substituted with an acetyl group and a disulfide bond is subsequently formed, and then a desired structure of etelcalcetide was obtained.

The present invention is described in more detail below with reference to some illustrative embodiments. It should be understood, however, that these embodiments serve only to facilitate understanding of the invention but not to restrict the scope of the invention. Unless otherwise specified, the reagents and instruments used in the embodiments are common commercially available products.

EXAMPLE 1

Preparation of Etelcalcetide

I. Step (a)

Rink amide resin (substitution ratio=0.606 mmol/g) as a solid support was weighed 16.502 g into reaction vessel with a sintered glass filter in the bottom, and swelled with freshly NMP (100 mL) for 1 hr prior to synthetic process. Once NMP was filtered out, the 400 mL solution of 20% piperidine/NMP was added to resin and mixed for 10 min for five times. The solution was subsequently filtered out and the resin was washed by freshly NMP (400 mL) for five times. While a Kaiser test performed a positive result, the Fmoc-deprotected sites available. Then, the solution of Fmoc-D-Arg(Pbf)-OH (6.49 g), BOP (13.27 g), and DIPEA (5.25 mL) in 400 mL NMP was mixed at room temperature for 5 hr. The reaction was monitored by Kaiser test, while the Kaiser test performed a negative result, the amino acid synthesis reaction was completed. If the result of Kaiser test was positive, the reaction was not completed and should subject to react for one more hour, and then the Kaiser test was performed for each of the amino acid coupling sub steps.

Once the amino acid synthesis reaction was completed, the resin was washed by 400 mL NMP as five times. The 400 mL solution of 20% piperidine/NMP was added to resin and mixed it for 10 min as five times. The solution was filtered out and the resin was washed by freshly NMP (400 mL) for five times. Then, the solution of Fmoc-D-Ala-OH (3.11 g), BOP (13.27 g), and DIPEA (5.25 mL) in 400 mL NMP was mixed at room temperature for 3 hr.

Applying the same process, it was completed the linear sequence consisting of 4 D-Arg, 2 D-Ala, and 1 D-Cys. Then, the 400 mL solution of 20% piperidine/NMP was added to resin and mixed it for 10 min for five times. The solution was filtered out and the resin was washed with freshly NMP (400 mL) for five times. The 400 mL solution consisted of NMP, Ac$_2$O, and pyridine (50/1/1) was introduced into resin and mixed at room temperature for 1 hr. The solution was filtered out and washed with freshly NMP (400 mL) for five times. As a result, the step (a) produced the sequence A with an acetylated N-terminal:

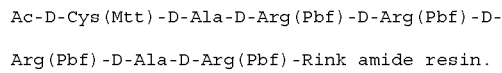

II. Step (b)

The 300 mL solution of TFA, TIPS, thioanisole, and DCM (3/10/2.5/84.5) was added into the sequence A and mixed for 10 min. Then, the solution was filtered out and repeated this procedure for five times. The solution was filtered out and washed with freshly NMP (400 mL) for three times. D-Cys in sequence without protecting group shown in the sequence B as below:

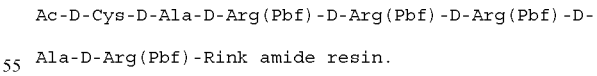

III. Step (c)

The solution of 4.505 g Boc-L-Cys(Npys)-OH, and 6.3 mL triethylamine in 400 mL NMP was mixed with the sequence B at room temperature for 2 hr. D-cys in sequence with linkage of disulfide bond to L-Cys shown the sequence C as below:

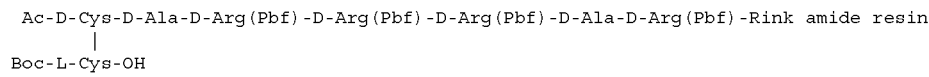

IV. Step (d)

The 300 mL solution of TFA, TIPS, thioanisole, and H₂O (85/10/2.5/2.5) was mixed with the sequence C at room temperature for 1 hr, which was cleaved from the resin and deprotected all of protecting groups in the side chain. Once filtered gathered, it was subjected to drop into 600 mL isopropylether to precipitate solid. After drying, it's a crude sample, being 98.3 yield and 72.9% purity, as a white solid (10.302 g). A sequence is desired as below:

```
Ac-D-Cys(L-Cys)-D-Ala-D-Arg-D-Arg-D-Arg-D-Ala-D-
Arg-NH₂.
```

The crude sample was subjected to chromatography, which removed organic solvent and most of H₂O by nanofiltration system, to give sample solution with 99% purity. If purity was below 99%, repeated the chromatography step again. A total yield was 50-60%.

EXAMPLE 2

Preparation of Etelcalcetide Hydrochloride

Sample solution of etelcalcetide from embodiment 1 was washed by 200 mL milli Q (T<10° C.) for six times, 200 mL 0.1% HCl$_{(aq)}$ (T<10° C.) for six times, and 200 mL milli Q (T<10° C.) for six times, respectively, in nanofiltration system, wherein its membrane was MWCO 300. Once the sample solution was collected, it was lyophilized to give white solid with 99% purity. Meanwhile, the yield loss in this process was below to 1%.

The impurities, which was acid form in C-terminal, amine-free sequence, and dimer, were below 0.1% in this process.

What is claimed is:

1. A method for synthesizing etelcalcetide of the following formula (I), consisting of the following steps:
   (a) using a solid support having a terminal with an amide group as a starting material in solid phase peptide synthesis under a base solution and sequentially synthesizing sequence A comprising protecting groups (PG) in the side chains of D-Cys and D Arg by Fmoc chemistry with a coupling reagent; deprotecting Fmoc groups with a deprotection solution and acetylating the N-terminal amino group of sequence A by adding an acetylation reagent with an equivalent ranging from 1 to 500 with pyridine;

Ac-D-Cys(PG)-D-Ala-D-Arg(PG)-D-Arg(PG)-D-Arg-(PG)-D-Ala-D-Arg(PG)-solid support (A);

(b) removing the protecting group in the side chain of D-Cys of the sequence A by adding an acid solution to obtain a sequence B;

Ac-D-Cys-D-Ala-D-Arg(PG)-D-Arg(PG)-D-Arg-(PG)-D-Ala-D-Arg(PG)-solid support (B);

(c) forming a disulfide at D-Cys of the sequence B with (PG)-L-Cys(PG)-OH to obtain a sequence C by adding a synthesis solution:

Ac-D-Cys-D-Ala-D-Arg(PG)-D-Arg(PG)-D-Arg-(PG)-D-Ala-D-Arg(PG)-solid support (PG)-L-Cys-OH (C); and (d) using a cleavage solution to remove the protecting groups of the sequence C and cleave the sequence C from the solid support to give etelcalcetide of formula (I):

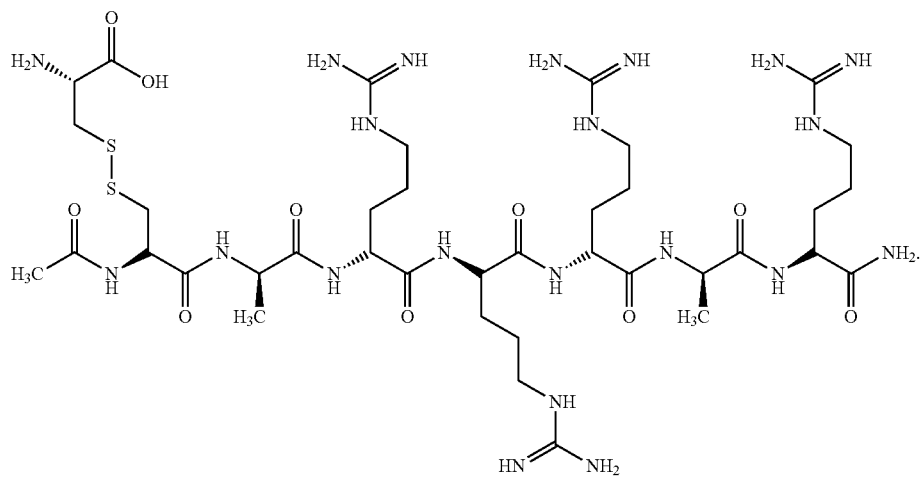

2. The method according to claim 1, wherein the solid support is selected from Rink amide resin, Rink amide AM resin, Rink amide MBHA resin, Wang resin, or 2-Chlorotrityl chloride resin with a substitution ratio as 0.1-1.5 mmol/g.

3. The method according to claim 1, wherein the protecting group in the side chain of D-Cys is 4-methyltrityl (Mtt), trityl (Trt), acetaminomethyl (acm), 3-nitro-2-pyridinesulphenyl (Npys), methylcarboxamide (cam), diphenylmethyl (Dpm), 4-methoxyb enzyl (Mob), S-tert-butylthio (StBu), methyl (me), sulfo (SO₃H), 2,4,6-trimethoxyphenylthio (STmp) or methylcarboxamide, and the protecting group of in the side chain of D-Arg is 2,2,4,6,7-pentamethyl-dihydrobenzofuran-5-sulfonyl (Pbf), tert-butoxycarbonyl (Boc), allyloxycarbonyl (Alloc), methyl (me), benzyloxycarbonyl (Z or Bz), 1,2-dimethylindole-3-sulfonyl (MIS), 2,2,5,7,8-pentamethylchroman-6-sulfonyl (Pmc), mesitylene-2-sulfonyl (Mts), or 4-methoxy-2,3,6-trimethylbenzenesulfonyl (Mtr).

4. The method according to claim 1, wherein the coupling reagent is selected from O-(benzotriazol-1-yl)-N,N,N ',N'-tetramethyluronium tetrafluoroborate (TBTU), N,N'-diisopropylcarbodiimide (DIC), 1-hydroxybenzotriazole hydrate (HOBt), O-(benzotriazol-1-yl)-N,N,N ',N'-tetramethyluronium hexafluorophosphate (HBTU), O-(6-chlorobenzotriazol-1-yl)-N,N,N ',N'-tetramethyluronium hexafluorophosphate (HCTU), benzotriazol-1-yl-oxytripyrrolidinophosphonium hexafluorophosphate (PyBOP), or benzotriazol-1-yloxytris(dimethylamino)phosphonium hexafluorophosphate (BOP).

5. The method according to claim 1, wherein the base solution is selected from dimethylformamide (DMF), N-methyl-2-pyrrolidone (NMP), diisopropylethylamine (DIPEA), N-methylmorpholine (NMM), trimethylamine (TEA), or pyridine.

6. The method according to claim 1, wherein the deprotection solution is selected from piperidine, diethylamine (DEA), or morpholine preparing in dimethylformamide (DMF), N-methyl-2-pyrrolidone (NMP), or dimethyl sulfoxide (DMSO) with a concentration ranging from 5% to 30%.

7. The method according to claim 1, wherein the acetylation reagent is selected from acetic anhydride ($Ac_2O$) or acetyl chloride prepared in dimethylformamide (DMF), N-methyl-2-pyrrolidone (NMP), or dimethyl sulfoxide (DMSO), and wherein the pyridine is of an equivalent ranging from 1 to 500.

8. The method according to claim 1, wherein the acid solution comprises trifluoroacetate (TFA), thioanisole, triisopropylsilane (TIPS), and methylene dichloride (DCM).

9. The method according to claim 1, wherein the synthesis solution is selected from diisopropylethylamine (DIPEA), N-methylmorpholine (NMM), or trimethylamine (TEA) prepared in dimethylformamide (DMF) or N-methyl-2-pyrrolidone (NMP).

10. The method according to claim 1, wherein the protecting group in N-terminal of (PG)-L-Cys(PG)-OH is t-butyloxycarbonyl (Boc) or fluorenylmethyloxycarbonyl (Fmoc), and a protecting group in a side chain of (PG)-L-Cys(PG)-OH is 3-nitro-2-pyridinesulphenyl (Npys) 4-methyltrityl (Mtt), trityl (Trt), acetaminomethyl (acm), methylcarboxamide (cam), diphenylmethyl (Dpm), 4-methoxybenzyl (Mob), S-tert-butylthio (StBu), methyl (me), sulfo ($SO_3H$), 2,4,6-trimethoxyphenylthio (STmp) or methylcarboxamide.

11. The method according to claim 1, wherein the cleavage solution in the step (d) comprises triisopropylsilane (TIPS), thioanisole, trifluoroacetate (TFA), and $H_2O$.

12. A method for synthesizing etelcalcetide hydrochloride, consisting of the following steps:
(a) using a solid support having a terminal with an amide group as a starting material in solid phase peptide synthesis and sequentially synthesizing sequence A comprising protecting groups (PG) in the side chains of D-Cys and D-Arg by Fmoc chemistry; deprotecting Fmoc groups and acetylating the N-terminal amino group of sequence A;
Ac-D-Cys(PG)-D-Ala-D-Arg(PG)-D-Arg(PG)-D-Arg-(PG)-D-Ala-D-Arg(PG)-solid support (A);
(b) removing the protecting group in the side chain of D-Cys of the sequence A to obtain a sequence B:
Ac-D-Cys-D-Ala-D-Arg(PG)-D-Arg(PG)-D-Arg-(PG)-D-Ala-D-Arg(PG)-solid support (B);
(c) forming a disulfide at D-Cys of the sequence B with (PG)-L-Cys(PG)-OH to obtain sequence C:
Ac-D-Cys-D-Ala-D-Arg(PG)-D-Arg(PG)-D-Arg-(PG)-D-Ala-D-Arg(PG)-solid support (PG)-L-Cys-OH (C); and
(d) using a cleavage solution to remove the protecting groups of the sequence C and cleave the sequence C from the solid support to give etelcalcetide of formula (I):

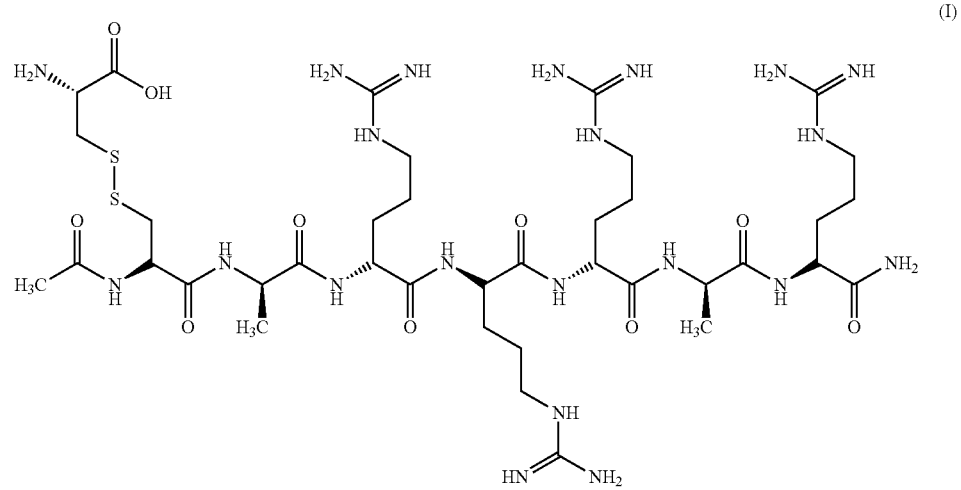

(e) adding a 0.01-10% HCl solution to form etelcalcetide hydrochloride.

* * * * *